United States Patent [19]

Shono

[11] Patent Number: 4,560,447
[45] Date of Patent: Dec. 24, 1985

[54] ELECTROLYTIC PROCESS FOR PREPARATION OF α-ALKYLATED ACETIC ACID DERIVATIVES

[75] Inventor: Tatsuya Shono, Kyoto, Japan

[73] Assignee: Otsuka Kagaku Kabushiki Kaisha, Osaka, Japan

[21] Appl. No.: 672,731

[22] Filed: Nov. 19, 1984

[30] Foreign Application Priority Data

Nov. 18, 1983 [JP] Japan ............... 58-218369

[51] Int. Cl.$^4$ ............................................. C25B 3/00
[52] U.S. Cl. ............................. 204/59 R; 204/72
[58] Field of Search ..................... 204/59 R, 72

[56] References Cited

U.S. PATENT DOCUMENTS 3,764,492 10/1973 Baizer ............... 204/59 R
4,132,611 1/1979 Baizer ............... 204/59 R
4,248,678 2/1981 Goodin ............. 204/59 R Primary Examiner—John F. Niebling
Attorney, Agent, or Firm—Armstrong, Nikaido, Marmelstein & Kubovcik

[57] ABSTRACT

This invention provides a process for preparing a α-alkylated acetic acid derivative represented by the formula $$Y-\underset{\underset{R'}{|}}{CH}-Z \qquad (II)$$

wherein Z is —COOR or —CN in which R is straight-chain or branched-chain alkyl, cycloalkyl, substituted or unsubstituted phenyl, or substituted or unsubstituted aralkyl, R' is substituted or unsubstituted straight-chain or branched-chain alkyl or alkenyl, and Y is an optionally substituted heterocyclic group or optionally substituted aromatic group, the process comprising subjecting an acetic acid derivative represented by the formula $$Y-CH_2-Z \qquad (I)$$

wherein Y and Z are as defined above to electrolytic reduction in the presence of an alkylating agent.

11 Claims, No Drawings

ELECTROLYTIC PROCESS FOR PREPARATION OF α-ALKYLATED ACETIC ACID DERIVATIVES

This invention relates to a process for preparing α-alkylated acetic acid derivatives.

This invention more particularly concerns with a process for preparing α-alkylated acetic acid derivatives represented by the formula $$Y-\underset{R'}{CH}-Z \qquad (II)$$

wherein Z is —COOR or —CN in which R is straight-chain or branched-chain alkyl, cycloalkyl, substituted or unsubstituted phenyl, or substituted or unsubstituted aralkyl, R' is substituted or unsubstituted straight-chain or branched-chain alkyl or alkenyl, and Y is an optionally substituted heterocyclic group or optionally substituted aromatic group, the substituents for the groups represented by Y being at least one species selected from the group consisting of hydroxyl, alkoxy, halogen, nitro, alkyl, alkenyl, alkylthio, alkenylthio, arylthio, heterocyclic thio group, cyclic tertiary amino, dialkylamino, alkenyloxy, substituted or unsubstituted aryl, substituted or unsubstituted aryloxy and substituted or unsubstituted aralkyloxy, the aromatic group or heterocyclic group, when having two or more adjacent substituents, optionally constituting a substituted or unsubstituted fused ring which may contain sulfur, oxygen and/or nitrogen.

The α-alkylated acetic acid derivatives of the formula (II) are known compounds which are useful as the intermediates for preparing pharmaceuticals such as anti-inflammatory agent or agricultural chemicals such as pyrethroid-type chemicals. Processes for preparing the α-alkylated acetic acid derivatives of the formula (II) are known. For example, the derivatives have been produced by activating the α-position of an acetic acid derivative of the formula $$Y-CH_2-Z \qquad (I)$$

wherein Y and Z are as defined above with metallic sodium in liquid ammonia and reacting the derivative with alkyl halide (Journal of Organic Chemistry, Vol. 28, pages 3108 to 3112 (1963)). However, the conventional process, when commercially carried out, encounters the disadvantages of requiring metallic sodium which is expensive, dangerous and difficult to handle and giving the derivatives of the formula (II) in relatively high but not always fully satisfactory yields.

An object of the present invention is to provide a process for preparing the desired α-alkylated acetic acid derivatives without use of a reactant such as metallic sodium which is dangerous and difficult to handle.

Another object of the invention is to provide a process for preparing the desired α-alkylated acetic acid derivatives in high yields.

These objects and other features of the present invention will become more apparent from the following description.

The present invention provides a process for preparing an α-alkylated acetic acid derivative represented by the formula $$Y-\underset{R'}{CH}-Z \qquad (II)$$

wherein Z is —COOR or —CN in which R is straight-chain or branched-chain alkyl, cycloalkyl, substituted or unsubstituted phenyl, or substituted or unsubstituted aralkyl, R' is substituted or unsubstituted straight-chain or branched-chain alkyl or alkenyl, and Y is an optionally substituted heterocyclic group or optionally substituted aromatic group, the substituents for the groups represented by Y being at least one species selected from the group consisting of hydroxyl, alkoxy, halogen, nitro, alkyl, alkenyl, alkylthio, alkenylthio, arylthio, heterocyclic thio group, cyclic tertiary amino, dialkylamino, alkenyloxy, substituted or unsubstituted aryl, substituted or unsubstituted aryloxy and substituted or unsubstituted aralkyloxy, the aromatic group or heterocyclic group, when having two or more adjacent substituents, optionally constituting a substituted or unsubstituted fused ring which may contain sulfur, oxygen and/or nitrogen, the process comprising subjecting an acetic acid derivative represented by the formula $$Y-CH_2-Z \qquad (I)$$

wherein Y and Z are as defined above to electrolytic reduction in the presence of an alkylating agent.

The process of the present invention does not require a special reactant, ensures safety in conducting the reaction and handling the starting materials and can produce the contemplated α-alkylated acetic acid derivative in very high yields.

The compounds of the formula (I) serving as one of the starting materials in the present process are known and easily available.

Examples of the groups represented by R in the formula (I) are as follows: exemplary of straight-chain or branched-chain alkyl groups are those having 1 to 6 carbon atoms, such as methyl, ethyl, propyl, n-butyl, t-butyl, n-hexyl, and the like; representative of the cycloalkyl groups are those having 5 to 6 carbon atom, such as cyclopentyl, cyclohexyl, and the like; illustrative of the substituted phenyl groups are those substituted with halogen, nitro, $C_1$–$C_5$ alkyl or $C_1$–$C_4$ alkoxy on the phenyl ring, such as p-chlorophenyl, p-methoxyphenyl, p-nitrophenyl, p-methylphenyl, p-isopropylphenyl, o-chlorophenyl, m-methylphenyl, and the like; and exemplary of the aralkyl groups are benzyl, diphenylmethyl, triphenylmethyl and benzyl substituted with halogen, $C_1$–$C_4$ alkoxy, nitro or $C_1$–$C_5$ alkyl on the phenyl ring, such as p-chlorobenzyl, p-methoxybenzyl, p-nitrobenzyl, p-methylbenzyl, p-isopropylbenzyl, and the like.

Examples of the groups represented by Y in the formula (I) are as follows: exemplary of the heterocyclic groups, are thienyl, furyl, pyridyl, pyrrolyl, oxazolyl, thiazolyl, thiadiazolyl, pyranyl, and the like; and representative of the aromatic groups are phenyl, naphthyl, anthranyl, tetralyl, and the like. The heterocyclic group and aromatic group represented by Y may be substituted with, for example, hydroxy; alkoxy having 1 to 6 carbon atoms which may be optionally substituted with halogen, such as methoxy, ethoxy, propoxy, isopropoxy, butoxy, t-butoxy, hexyloxy, trichloromethoxy, difluoromethoxy and the like; alkyl having 1 to 6 carbon atoms, such as methyl, ethyl, propyl, isopropyl, butyl, isobutyl, t-butyl, hexyl and the like; alkenyl having 3 to 6 carbon atoms, such as propenyl, butenyl, isoprenyl, pentenyl, hexenyl and the like; nitro; halogen such as chlorine, bromine, iodine, fluorine and the like; alkylthio having 1 to 6 carbon atoms, such as methylthio, ethylthio, propylthio, hexylthio and the like; alkenylthio having 3 to 6 carbon atoms, such as allylthio, butenylthio and the like; arylthio such as phenylthio and phenylthio substituted with halogen, $C_1$–$C_4$ alkoxy or nitro on the phenyl ring, e.g., p-methoxyphenylthio, p-nitrophenylthio, p-chlorophenylthio and the like; heterocyclic thio groups, such as oxazolylthio, thienylthio, thiazolylthio, thiadiazolylthio, pyridylthio, furylthio and the like; cyclic tertiary amino such as 1-oxo-2-isoindolinyl, pyrrolinyl and the like; di($C_1$–$C_6$ alkyl)amino, such as dimethylamino, diethylamino, dibutylamino, methylethylamino and the like; alkenyloxy having 3 to 6 carbon atoms, such as allyloxy, 1-butenyloxy, 2-butenyloxy, isobutenyloxy and the like; substituted or unsubstituted aryl, such as phenyl, phenyl substituted with $C_1$–$C_5$ alkoxy, $C_3$–$C_5$ alkenyloxy, benzyloxy, nitro, halogen, hydroxy, $C_1$–$C_5$ alkyl or $C_1$–$C_2$ alkylenedioxy on the phenyl ring, e.g., p-methoxyphenyl, p-butoxyphenyl, p-allyloxyphenyl, p-benzyloxyphenyl, p-nitrophenyl, p-chlorophenyl, p-hydroxyphenyl, o-chlorophenyl, m-nitrophenyl, o-ethoxyphenyl, 3,4-dimethoxyphenyl, 3,4-methylenedioxyphenyl, 3-chloro-4-allyloxyphenyl, 3-chloro-4-butoxyphenyl, p-bromophenyl, p-isobutylphenyl, p-isopropylphenyl and the like; substituted or unsubstituted aryloxy such as unsubstituted phenoxy, phenoxy substituted with $C_1$–$C_4$ alkoxy, nitro, halogen or $C_1$–$C_5$ alkyl on the phenyl ring, e.g., p-methoxyphenoxy, p-nitrophenoxy, p-chlorophenoxy, p-methylphenoxy, p-isopropylphenoxy and the like; substituted or unsubstituted aralkyloxy, such as diphenylmethyloxy and phenyl-$C_1$–$C_3$ alkyloxy optionally substituted with $C_1$–$C_5$ alkoxy or halogen on the phenyl ring. e.g., benzyloxy, p-methoxybenzyloxy, p-chlorobenzyloxy, phenylethyloxy, phenylpropyloxy and the like. Examples of the substituted or unsubstituted fused ring group which may be constituted by the aromatic or heterocyclic ring having two or more adjacent substituents and which may optionally contain sulfur, oxygen and/or nitrogen atom are benzoxazolyl, benzothiazolyl, dibenzoxepinyl, benzopyranopyridyl, dihydrobenzopyranyl, tetrahydrobenzopyranyl, quinolyl, phenothiazinyl, benzofuranyl, carbazolyl, dihydrodibenzothiepinyl, fluorenyl, indanyl and the like which may be substituted with halogen or $C_1$–$C_4$ alkyl.

Representative examples of the substituted or unsubstituted heterocyclic groups represented by Y are thienyl, furyl, 5-methylfuryl, pyridyl, picolyl, pyrrolyl, oxazolyl, thiazolyl, thiadiazolyl, pyranyl and the like. Representative examples of the substituted or unsubstituted aromatic groups represented by Y are phenyl, tolyl, p-methoxyphenyl, p-butoxyphenyl, p-allyloxyphenyl, p-benzyloxyphenyl, p-nitrophenyl, p-chlorophenyl, p-hydroxyphenyl, o-chlorophenyl, m-nitrophenyl, o-ethoxyphenyl, 3,4-dimethoxyphenyl, 3,4-methylenedioxyphenyl, 3-chloro-4-allyloxyphenyl, 3-chloro-4-butoxyphenyl, p-bromophenyl, p-isobutylphenyl, p-isopropylphenyl, naphthyl, 6-methoxynaphthyl, m-phenoxyphenyl, p-difluoromethoxyphenyl, o-phenoxyphenyl, p-phenoxyphenyl, anthranyl, tetralyl, p-dimethylaminophenyl, p-phenyl-phenyl, o-(2,4-dichloro-phenoxy)-phenyl, p-(4-chloro-benzyloxy)-benzyl, 1-oxo-2-isoindolinyl-phenyl, p-(1-pyrrolinyl)-m-chloro-phenyl, p-phenylthiophenyl and the like. Representative examples of the fused ring groups represented by Y are benzoxazolyl, benzothiazolyl, N-methylphenothiazinyl, carbazolyl, 6-chloro-carbazolyl, dibenzoxepinyl, benzopyranopyridyl, dihydrobenzopyranyl, tetrahydrobenzopyranyl, benzofuranyl, quinolyl, 9H-fluorenyl, 2-isopropyl-5-indanyl, dihydrobenzothiepinyl and the like.

Examples of the alkylating agent which can be used in the present invention include a wide range of compounds, particularly those capable of introducing $C_1$–$C_6$ alkyl to the α-position of the compound (I), such as alkyl ester of methanesulfonic acid, e.g., methyl methanesulfonate, ethyl methanesulfonate, isopropyl methanesulfonate, butyl methanesulfonate and the like; mono- and di-alkyl sulfate, e.g., dimethyl sulfate, diethyl sulfate, diisopropyl sulfate, monomethylsulfate, monoethyl sulfate, monoisopropyl sulfate, and the like; alkyl halide, e.g., methyl chloride, methyl bromide, methyl iodide, ethyl chloride, ethyl bromide, ethyl iodide, isopropyl chloride, isopropyl bromide, isopropyl iodide, butyl chloride, butyl bromide, butyl iodide, hexyl chloride, hexyl bromide, hexyl iodide and the like; trialkyl phosphate, such as trimethyl phosphate, triethyl phosphate, tripropyl phosphate, tributyl phosphate, trihexyl phosphate and the like; alkyl ester of benzenesulfonic acid, e.g., methyl benzenesulfonate, ethyl benzenesulfonate, isopropyl benzenesulfonate, butyl benzenesulfonate, hexyl benzenesulfonate, methyl p-methylbenzenesulfonate, ethyl p-methyl-benzenesulfonate, butyl p-methyl-benzenesulfonate and the like; alkyl orthoformate, e.g., methyl orthoformate, ethyl orthoformate, propyl orthoformate and the like; 2,2-dialkoxyalkane, such as 2,2-dimethoxypropane, 2,2-diethoxypropane, 2,2-dibutoxypropane, 2,2-dimethoxybutane, 2,2-diethoxybutane and the like. The alkylating agent useful in the present invention includes not only the foregoing compounds which can add $C_1$–$C_6$ alkyl to the compound (I), but also those which can introduce substituted $C_1$–$C_5$ alkyl or $C_3$–$C_6$ alkenyl to the α-position of the compound (I), i.e., substituted $C_1$–$C_5$ alkyl halide or $C_3$–$C_6$ alkenyl halide. The term "alkylating agent" as used throughout the specification and claims also includes the substituted $C_1$–$C_5$ alkyl halide or $C_3$–$C_6$ alkenyl halide. Examples of the substituted alkyl halide useful in the present invention are aralkyl halide, such as diphenyl bromide, benzyl halide optionaly substituted with $C_1$–$C_5$ alkoxy or nitro on the phenyl ring, e.g., benzyl bromide, benzyl chloride, benzyl iodide, p-methoxybenzyl chloride, p-nitrobenzyl bromide, etc.; $C_1$–$C_3$ alkoxy-substituted $C_1$–$C_5$ alkyl halide, such as methoxymethyl bromide, ethoxyethyl iodide, methoxybutyl bromide, etc.; phenoxy-substituted $C_1$–$C_3$ alkyl halide, such as phenoxymethyl chloride, phenoxybutyl bromide, etc. Examples of $C_3$–$C_6$ alkenyl halide are allyl chloride, allyl bromide, allyl iodide, 2-butenyl bromide, isobutenyl chloride, 2-pentenyl chloride, etc. There is no particular restriction as to the amount of the alkylating agent as used in the present invention, but a suitable amount is usually in the range of about 1 to about 10 moles per mole of the compound of the formula (I). According to the present invention, the alkyl or substituted alkyl group or alkenyl group corresponding to the type of alkylating agent used is introduced as the α-substituent R' of the formula (II). Thus the substituent R' represents $C_1$–$C_6$ alkyl, benzyl optionally substituted with $C_1$–$C_5$ alkoxy or nitro on the phenyl ring, diphenylmethyl, $C_1$-$C_3$ alkoxy-substituted $C_1$-$C_5$ alkyl and phenoxy-substituted $C_1$-$C_3$ alkyl, and $C_3$-$C_6$ alkenyl.

The electrolytic reduction in the present invention is usually conducted in a suitable solvent. Generally aprotic organic polar solvents are preferred. Examples of useful aprotic organic polar solvents are amides such as dimethylformamide, diethylformamide, dimethylacetamide, diethylacetamide and the like; nitriles such as acetonitrile, propionitrile, butyronitrile and the like; dimethylsulfoxide: hexamethylphoshoramide; N-methylpyrrolidone and the like. The aprotic polar organic solvent can be used in mixture with an inert solvent such as pentane, hexane, benzene, toluene, cyclohexane, ethyl ether, tetrahydrofuran, dioxane and like ethers.

It is preferred in the present invention to carry out the electrolytic reduction in the presence of a supporting electrolyte. Examples of useful supporting electrolyte include quaternary ammonium salt, alkali metal salt, alkaline earth metal salt, etc. Examples of the cationic component of the supporting electrolyte are tetra ($C_1$-$C_4$ alkyl)ammonium cations such as tetramethylammonium, tetraethylammonium, tetrabutylammonium, trimethylmonoethylammonium, trimethylmonobutylammonium, and lithium, sodium, potassium, magnesium, calcium, etc. Examples of the anionic component of the supporting electrolyte are halogen anions such as chlorine, bromine, iodine and the like, nitrate anion, perchlorate anion, periodate anion, sulfate anion, borofluorate anion, sulfonate anion, e.g., benzenesulfonate anion, p-toluenesulfonate anion and the like. The amount of the supporting electrolyte as used in the present invention is not particularly limited, but is preferably in the range of about 0.01 to about 50 mols per mol of the compound of the formula (I).

The electrolysis of the present invention can be performed at either controlled potential or constant current. The electrolytic cell which can be employed in the present invention is not limited to a particular type and any suitable conventional cell can be used with due efficiency. Preferred examples, however, are those of the diaphragm type in which the electrolytic cell is divided into an anode chamber and cathode chamber by a diaphragm. Useful diaphragms are not restricted to a particular kind and can be any of asbestos diaphragm, glass filter, ceramic filter, porous porcelain, ion exchange membrane, etc. The temperature range in which the electrolysis of the present invention can be effected is not particularly limitative, but preferably about $-30°$ to about 80° C. Useful electrodes can be made of any conventional materials, such as platinum, carbon, titanium, lead, copper, stainless steel, iron, etc. Usually controlled potential electrolysis or constant current electrolysis according to the present invention can be performed at a current density of about 0.005 to about 5 A/cm$^2$. In either case, about 1.05 to about 3 F of electricity per mol of the compound of the formula (I) is passed.

The compounds of the formula (II) obtained by the process of the present invention can be separated or purified by conventional methods such as extraction, distillation, recrystallization, column chromatography or the like.

The present invention will be described below in more detail with reference to the following Examples in which the hydrolysate (free acid) produced together with the desired compound of the formula (II) is quantatively converted into the compound of the formula (II) by a conventional esterification process.

EXAMPLE 1

Into the cathode chamber of an electrolytic cell divided with an ion-exchange resin diaphragm was placed a solution of 10 mmols of methyl phenylacetate, 12 mmols of methyl methanesulfonate and 1.0 g of tetraethylammonium tosylate in 30 ml of anhydrous dimethylformamide. And the anode chamber of the electrolytic cell was supplied with a solution of 3.0 g of tetraethylammonium tosylate in 10 ml of anhydrous dimethylformamide. Constant current electrolysis was conducted at 0.2 A/cm$^2$ with use of platinum for both the anode and cathode. After passing 1.5 F of electricity per mol of the methyl phenylacetate through the solution at room temperature, the cathode solution was added to a saturated aqueous solution of ammonium chloride and the mixture was extracted twice with ether. The ether was removed by distillation and the residue was purified by silica gel column chromatography using hexane-ethyl acetate (10:1), giving methyl α-methylphenylacetate in a yield of 78% and α-methylphenylacetic acid in a yield of 15%. The spectral data of the ester were as follows.

IR (neat) (cm$^{-1}$) 3050, 3000, 2970, 1730, 1180.

NMR (CCl$_4$)(δ) 1.42 (d, 3H, J=7.0 Hz), 3.54 (s,3H), 3.60 (q, 1H, J=7.0 Hz), 7.23 (s, 5H).

EXAMPLE 2

Into the cathode chamber of an electrolytic cell divided with an ion-exchange resin diaphragm was placed a solution of 10 mmols of methyl phenylacetate, 12 mmols of ethyl methanesulfonate and 1.0 g of tetraethylammonium tosylate in 30 ml of anhydrous dimethylformamide. And the anode chamber was provided with a solution of 1.0 g of tetraethylammonium tosylate in 10 ml of anhydrous dimethylformamide. Constant current electrolysis was performed at 0.2 A/cm$^2$ with use of platinum for the cathode and carbon for the anode. After passing 1.5 F of electricity per mol of the methyl phenylacetate through the solution at 5 to 10 C, the cathode solution was added to a saturated aqueous solution of ammonium chloride and the mixture was extracted twice with ether. The ether was distilled off and the residue was purified by silica gel column chromatography using hexane-ethyl acetate (10:1), giving methyl α-ethylphenylacetate in a yield of 77% and α-ethylphenylacetic acid in a yield of 13%. The spectral data of the ester were as follows.

IR (neat) (cm$^{-1}$) 2970, 1740, 1170.

NMR (CCl$_4$) (δ) 0.88 (t, 3H, J=7.5 Hz), 1.50-2.30 (m, 2H), 3.47 (t, 1H, J=7.5 Hz), 3.67 (s, 3H), 7.33 (s, 5H).

EXAMPLE 3

Into the cathode chamber of an electrolytic cell divided with a diaphragm (asbestos) was placed a solution of 10 mmols of methyl phenylacetate, 12 mmols of isopropyl bromide and 1.0 g of tetramethylammonium tosylate in 30 ml of anhydrous dimethylformamide. Constant current electrolysis was conducted at 0.2 A/cm$^2$ with use of lead for the anode and carbon for the cathode. After passing 1.5 F of electricity per mol of the methyl phenylacetate at 20° to 25° C., the cathode solution was added to a saturated aqueous solution of ammonium chloride and the mixture was extracted twice with ether. The ether was distilled off and the residue was purified by silica gel column chromatography using hexane-ethyl acetate (10:1), giving methyl α-isopropylphenylacetate in a yield of 80% and α-isopropylphenylacetic acid in a yield of 9%. The spectral data of the ester were as follows.

IR (neat) (cm$^{-1}$) 2970, 1735, 1160.

NMR (CCl$_4$)(δ) 0.69 (d, 3H, J=6.0 Hz), 1.00 (d, 3H, J=1.00 Hz), 2.10–2.50 (m, 1H), 3.06 (d, 1H, J=10.5 Hz), 3.59 (s, 3H), 7.28 (s, 5H).

EXAMPLE 4

Into the cathode chamber of an electrolytic cell divided with a diaphragm (ceramic filter) was placed a solution of 10 mmols of methyl p-methoxyphenylacetate, 12 mmols of methyl iodide and 2.0 g of tetraethylammonium perchlorate in 30 ml of anhydrous dimethylacetamide. And the anode chamber was provided with a solution of 3.0 g of tetraethylammonium perchlorate in 20 ml of anhydrous dimethylformamide. Constant current electrolysis was performed at 0.2 A/cm$^2$ with use of platinum for both the anode electrode and the cathode electrode. After passing 1.5 F of electricity per mol of the methyl p-methoxyphenylacetate through the solution at −5° to 0° C., the cathode solution was added to a saturated aqueous solution of ammonium chloride and the mixture was extracted twice with ether. The ether was distilled off and the residue was purified by silica gel column chromatography using hexane-ethyl acetate (10:1), giving methyl α-methyl-p-methoxyphenylacetate in a yield of 81% and α-methyl-p-methoxyphenylacetic acid in a yield of 10%. The spectral data of the ester were as follows.

IR (neat) (cm$^{-1}$) 2950, 1740, 1240.

NMR (CCl$_4$) (δ) 1.42 (d, 3H, J=7.0 Hz), 3.54 (q, 2H, J=7.0 Hz), 3.60 (s, 3H), 3.74 (s, 3H), 6.76 (d, 2H, J=7.0 Hz), 7.14 (d, 2H, J=7.0 Hz).

EXAMPLE 5

Into the cathode chamber of an electrolytic cell divided with an ion-exchange resin diaphragm was placed a solution of 10 mmols of methyl 1-naphthylacetate, 12 mmols of dimethyl sulfate and 1.0 g of tetraethylammonium tosylate in 30 ml of acetonitrile. The anode chamber was supplied with a solution of 2.0 g of tetraethylammonium tosylate in 10 ml of acetonitrile. Constant current electrolysis was conducted at 0.2 A/cm$^2$ with use of platinum for both the cathode and the anode. After passing 1.5 F of electricity per mol of the methyl 1-naphthylacetate at room temperature, the cathode solution was added to a saturated aqueous solution of ammonium chloride and the mixture was extracted twice with ether. The ether was distilled off and the residue was purified by silica gel column chromatography using hexane-ethyl acetate (10:1), giving methyl 1-naphthyl(α-methyl)acetate in a yield of 92%. The spectral data of the ester were as follows.

IR (neat) (cm$^{-1}$) 3050, 3000, 1740.

NMR (CCl$_4$) (δ) 1.60 (d, 3H, J=7.0 Hz), 3.60 (s, 3H), 4.41(q, 1H, J=7.0 Hz), 7.30–8.10(m, 7H).

EXAMPLE 6

The same reaction and the same treatment as in Example 1 were followed by using methyl p-benzyloxyphenyl acetate and methyl benzenesulfonate, producing methyl p-benzyloxy(α-methyl)phenylacetate in a yield of 80% and p-benzyloxy(α-methyl)phenylacetic acid in a yield of 8%. The spectral data of the ester were as follows.

IR (neat) (cm$^{-1}$) 1735, 1610, 1510, 1240.

NMR (CCl$_4$) (δ) 1.42 (d, 3H, J=7.0 Hz), 3.57 (s, 3H), 3.57 (q, 4H, J=7.0 Hz), 5.00 (s, 2H), 7.00(dd, 4H), 7.34 (s, 5H).

EXAMPLE 7

The same reaction and the same treatment as in Example 1 were followed using methyl p-chlorophenylacetate and methyl bromide, producing methyl p-chloro(α-methyl)phenylacetate in a yield of 83% and p-chloro(α-methyl)phenylacetic acid in a yield of 5%. The spectral data of the ester were as follows.

IR (neat) (cm$^{-1}$) 1740, 1500, 1210, 1170.

NMR (CCl$_4$) (δ) 1.43 (d, J=6.8 Hz), 3.60 (s, 3H), 3.61 (q, J=6.8 Hz), 7.23 (s, 4H).

Following the general procedure of Example 1 and using the starting materials, alkylating agent, supporting electrolyte and solvent as shown below in Table 1, compounds of the formula (II) were prepared. Table 2 below indicates the reaction temperatures, electrodes, reaction products, and yields. The structures of the reaction products were confirmed by IR and NMR as in Example 1. The solvent code in Table 1 is as follows.

DMF: Dimethylformamide
THF: Tetrahydrofuran
HMPA: Hexamethylphoshoramide

TABLE 1

| Example No. | Starting material | Alkylating agent | Supporting electrolyte | Solvent |
| --- | --- | --- | --- | --- |
| 8 | ⟨phenyl⟩—CH$_2$COOCH$_3$ | CH$_3$I | Tetraethylammonium tosylate | DMF |
| 9 | ⟨phenyl⟩—CH$_2$COOCH$_3$ | ⟨phenyl⟩—SO$_3$CH$_3$ | Tetraethylammonium tosylate | DMF |
| 10 | ⟨phenyl⟩—CH$_2$COOCH$_3$ | CH$_3$SO$_3$CH$_3$ | Tetraethylammonium tosylate | DMF + THF |

TABLE 1-continued

| Example No. | Starting material | Alkylating agent | Supporting electrolyte | Solvent |
|---|---|---|---|---|
| 11 | C6H5—CH2COOCH3 | (CH3)3PO4 | Tetraethylammonium tosylate | DMF |
| 12 | C6H5—CH2COOCH3 | CH3SO3CH3 | Tetraethylammonium perchlorate | DMF |
| 13 | C6H5—CH2COOCH3 | CH3SO3CH3 | Tetraethylammonium tosylate | DMF |
| 14 | NO2—C6H4—CH2COOCH3 | CH3SO3CH3 | Tetraethylammonium tosylate | DMF |
| 15 | CH3—C6H4—CH2COOCH3 | CH3SO3CH3 | Tetraethylammonium tosylate | DMF + n-hexane |
| 16 | (CH3)2N—C6H4—CH2COOCH3 | CH3SO3CH3 | Tetraethylammonium tosylate | HMPA |
| 17 | Cl—C6H4—CH2COOC2H5 | CH3I | Tetraethylammonium tosylate | DMF |
| 18 | C6H5CH2O—C6H4—CH2COOCH3 | (CH3)2CHCH2Br | Tetraethylammonium tosylate | DMF |
| 19 | C6H5—O—C6H4—CH2COOCH3 | CH3SO3CH3 | Tetraethylammonium tosylate | DMF |
| 20 | CH3O—C6H4—CH2COOCH3 | (CH3)2CHBr | Tetraethylammonium tosylate | DMF |
| 21 | CH2=CHCH2O—C6H3(Cl)—CH2COOCH3 | CH3SO3CH3 | Tetraethylammonium tosylate | DMF |
| 22 | (CH3)2CHCH2—C6H4—CH2COOCH3 | CH3I | Tetraethylammonium tosylate | DMF |

TABLE 1-continued

| Example No. | Starting material | Alkylating agent | Supporting electrolyte | Solvent |
|---|---|---|---|---|
| 23 | pyridine-CH₂COOCH₃ | CH₃SO₃CH₃ | Tetraethylammonium tosylate | DMF |
| 24 | furan-CH₂COOCH₃ | CH₃SO₃CH₃ | Tetraethylammonium tosylate | DMF |
| 25 | benzoxazole-CH₂COOCH₃ | CH₃I | Tetraethylammonium tosylate | DMF |
| 26 | (benzophenone derivative)-CH₂COOCH₃ | (CH₃)₂SO₄ | Tetraethylammonium tosylate | DMF |
| 27 | (substituted aniline)-CH₂COOCH₃ | CH₃SO₃CH₃ | Tetraethylammonium tosylate | DMF |
| 28 | quinoline-CH₂COOCH₃ | CH₃SO₃CH₃ | Tetraethylammonium tosylate | DMF |
| 29 | biphenyl-CH₂COOCH₃ | CH₃I | Tetraethylammonium tosylate | DMF |
| 30 | C₆H₅-CH₂COO-cyclohexyl | CH₃I | Tetraethylammonium tosylate | DMF |
| 31 | C₆H₅-CH₂COOCH₂-C₆H₅ | CH₃I | Tetraethylammonium tosylate | DMF |
| 32 | C₆H₅-CH₂COOCH₂-C₆H₄-OCH₃ | CH₃I | Tetraethylammonium tosylate | DMF |
| 33 | C₆H₅-CH₂COO-C₆H₅ | CH₃I | Tetraethylammonium tosylate | DMF |
| 34 | C₆H₅-CH₂COOCH₃ | CH₂=CHCH₂Br | Tetraethylammonium tosylate | DMF |

TABLE 1-continued

| Example No. | Starting material | Alkylating agent | Supporting electrolyte | Solvent |
|---|---|---|---|---|
| 35 | 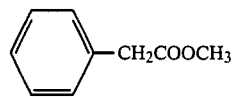 | CH₃OCH₂CH₂Br | Tetraethylammonium tosylate | DMF |
| 36 | 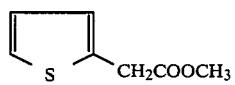 | CH₃I | Tetraethylammonium tosylate | DMF |
| 37 | 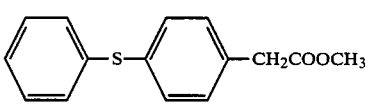 | CH₃I | Tetraethylammonium tosylate | DMF |
| 38 | 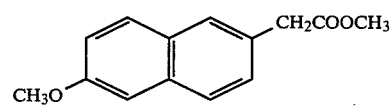 | CH₃I | Tetraethylammonium tosylate | DMF |
| 39 | 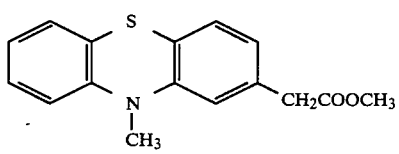 | CH₃I | Tetraethylammonium tosylate | DMF |
| 40 | 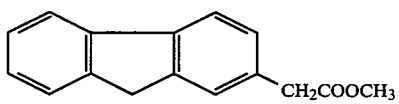 | CH₃I | Tetraethylammonium tosylate | DMF |
| 41 | 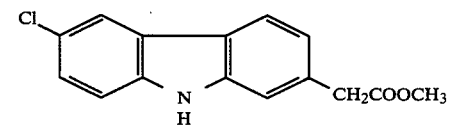 | CH₃I | Tetraethylammonium tosylate | DMF |
| 42 | 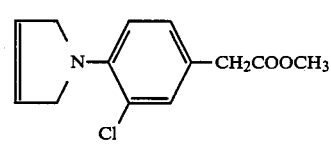 | CH₃I | Tetraethylammonium tosylate | DMF |
| 43 | 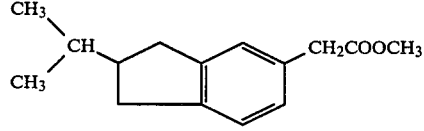 | CH₃I | Tetraethylammonium tosylate | DMF |
| 44 | 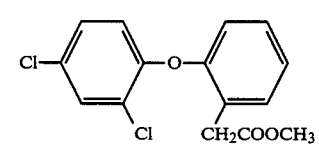 | CH₃I | Tetraethylammonium tosylate | DMF |
| 45 | 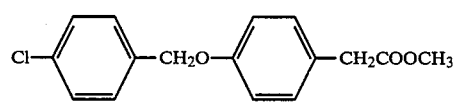 | CH₃I | Tetraethylammonium tosylate | DMF |

TABLE 2
| Example No. | Reaction Temp. | Electrode | Product | Yield (%) |
|---|---|---|---|---|
| 8 | room temperature | Pt—Pt | 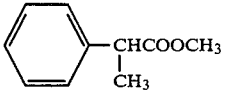 | 84 |
|  |  |  | 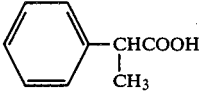 | 7 |
| 9 | room temperature | Pt—Pt | 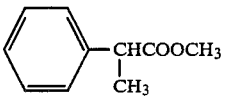 | 75 |
|  |  |  | 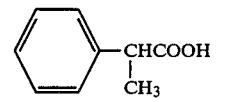 | 11 |
| 10 | 20 to 25° C. | Pt—C | 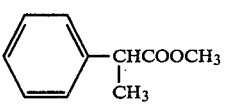 | 82 |
|  |  |  | 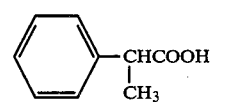 | 8 |
| 11 | room temperature | Pt—Pt | 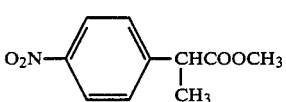 | 71 |
|  |  |  | 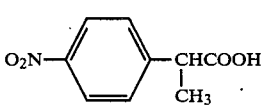 | 9 |
| 12 | 0 to 10° C. | Pt—Pt | (PhCH(CH₃)COOCH₃) | 89 |
|  |  |  | (PhCH(CH₃)COOH) | 3 |
| 13 | −20 to −10° C. | Pt—Pt | (PhCH(CH₃)COOCH₃) | 94 |
| 14 | room temperature | Pt—Pt | (O₂N-C₆H₄-CH(CH₃)COOCH₃) | 80 |
|  |  |  | (O₂N-C₆H₄-CH(CH₃)COOH) | 7 |

TABLE 2-continued
| Example No. | Reaction Temp. | Electrode | Product | Yield (%) |
|---|---|---|---|---|
| 15 | room temperature | Pt—Pt | 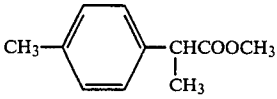 | 83 |
|  |  |  | 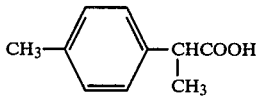 | 7 |
| 16 | room temperature | Pt—Pt | 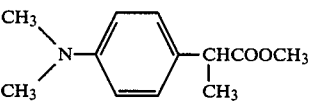 | 81 |
|  |  |  | 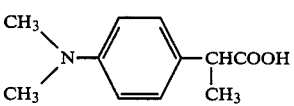 | 10 |
| 17 | room temperature | Pt—Pt | 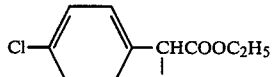 | 83 |
|  |  |  | 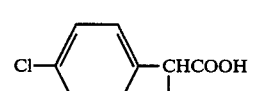 | 7 |
| 18 | room temperature | Pt—Pt | 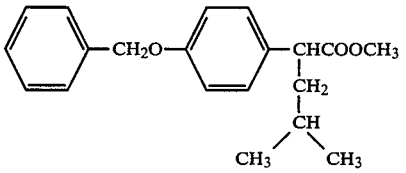 | 83 |
|  |  |  | 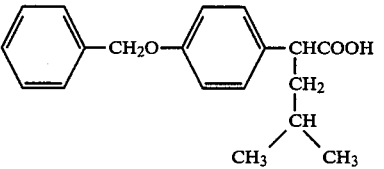 | 9 |
| 19 | room temperature | Pt—Pt | 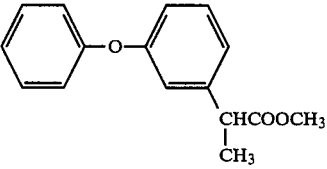 | 81 |
|  |  |  | 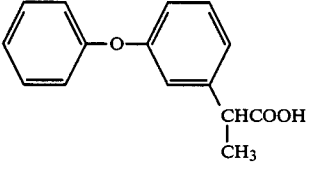 | 10 |

TABLE 2-continued
| Example No. | Reaction Temp. | Electrode | Product | Yield (%) |
|---|---|---|---|---|
| 20 | room temperature | Pt—Pt | 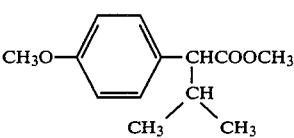 | 84 |
|  |  |  | 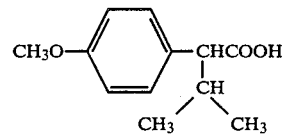 | 8 |
| 21 | room temperature | Pt—Pt | 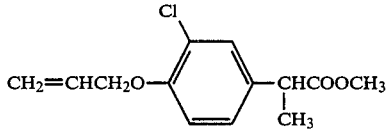 | 80 |
|  |  |  | 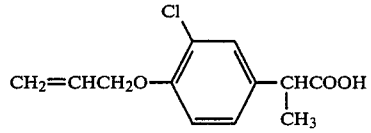 | 10 |
| 22 | room temperature | Pt—Pt | 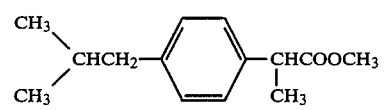 | 85 |
|  |  |  | 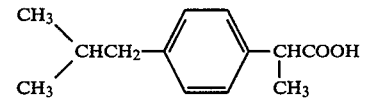 | 7 |
| 23 | room temperature | Pt—Pt | 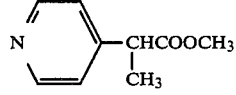 | 79 |
|  |  |  | 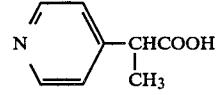 | 9 |
| 24 | room temperature | Pt—Pt | 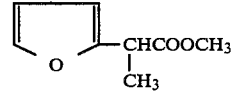 | 81 |
|  |  |  | 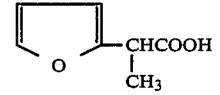 | 7 |
| 25 | room temperature | Pt—Pt | 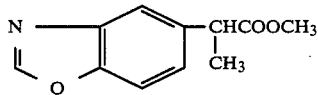 | 80 |
|  |  |  | 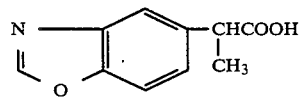 | 9 |

TABLE 2-continued
| Example No. | Reaction Temp. | Electrode | Product | Yield (%) |
|---|---|---|---|---|
| 26 | room temperature | Pt—Pt | 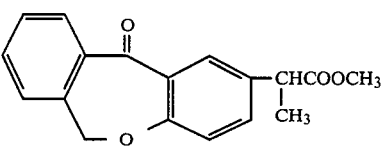 | 80 |
|  |  |  | 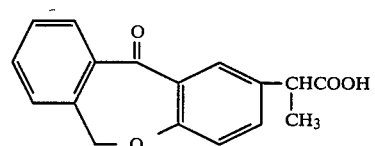 | 9 |
| 27 | room temperature | Pt—Pt | 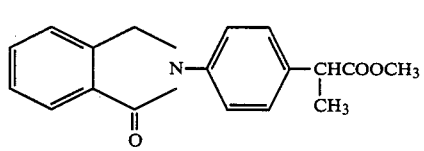 | 83 |
|  |  |  | 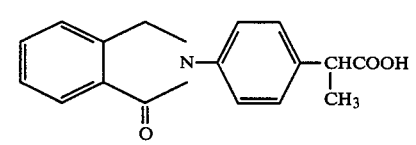 | 7 |
| 28 | room temperature | Pt—Pt | 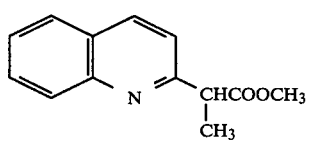 | 78 |
|  |  |  | 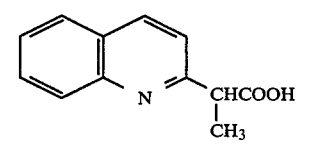 | 11 |
| 29 | room temperature | Pt—Pt | 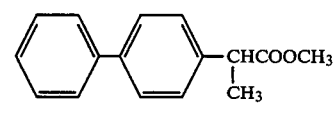 | 81 |
|  |  |  | 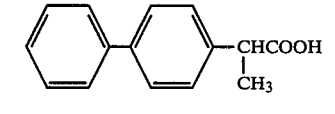 | 9 |
| 30 | room temperature | Pt—Pt | 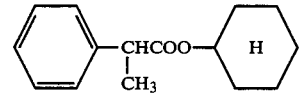 | 80 |
|  |  |  | 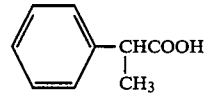 | 12 |
| 31 | room temperature | Pt—Pt | 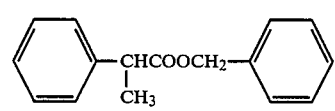 | 80 |

TABLE 2-continued

| Example No. | Reaction Temp. | Electrode | Product | Yield (%) |
|---|---|---|---|---|
| | | | Ph-CH(CH₃)-COOH | 13 |
| 32 | room temperature | Pt—Pt | Ph-CH(CH₃)-COOCH₂-C₆H₄-OCH₃ | 79 |
| | | | Ph-CH(CH₃)-COOH | 15 |
| 33 | room temperature | Pt—Pt | Ph-CH(CH₃)-COO-Ph | 82 |
| | | | Ph-CH(CH₃)-COOH | 8 |
| 34 | room temperature | Pt—Pt | Ph-CH(CH₂CH=CH₂)-COOCH₃ | 76 |
| | | | Ph-CH(CH₂CH=CH₂)-COOH | 8 |
| 35 | room temperature | Pt—Pt | Ph-CH(CH₂CH₂OCH₃)-COOCH₃ | 79 |
| | | | Ph-CH(CH₂CH₂OCH₃)-COOH | 8 |
| 36 | room temperature | Pt—Pt | (2-thienyl)-CH(CH₃)-COOCH₃ | 85 |
| | | | (2-thienyl)-CH(CH₃)-COOH | 7 |
| 37 | room temperature | Pt—Pt | Ph-S-C₆H₄-CH(CH₃)-COOCH₃ | 73 |
| | | | Ph-S-C₆H₄-CH(CH₃)-COOH | 9 |

TABLE 2-continued

| Example No. | Reaction Temp. | Electrode | Product | Yield (%) |
|---|---|---|---|---|
| 38 | room temperature | Pt—Pt | 6-methoxy-naphthalen-2-yl-CH(CH₃)COOCH₃ | 82 |
| | | | 6-methoxy-naphthalen-2-yl-CH(CH₃)COOH | 8 |
| 39 | room temperature | Pt—Pt | phenothiazine(N-CH₃) derivative-CH(CH₃)COOCH₃ | 78 |
| | | | phenothiazine(N-CH₃) derivative-CH(CH₃)COOH | 9 |
| 40 | room temperature | Pt—Pt | fluoren-2-yl-CH(CH₃)COOCH₃ | 86 |
| | | | fluoren-2-yl-CH(CH₃)COOH | 6 |
| 41 | room temperature | Pt—Pt | 6-chloro-carbazol-2-yl-CH(CH₃)COOCH₃ | 77 |
| | | | 6-chloro-carbazol-2-yl-CH(CH₃)COOH | 8 |
| 42 | room temperature | Pt—Pt | 4-(pyrrolin-1-yl)-3-chlorophenyl-CH(CH₃)COOCH₃ | 79 |
| | | | 4-(pyrrolin-1-yl)-3-chlorophenyl-CH(CH₃)COOH | 9 |

TABLE 2-continued

| Example No. | Reaction Temp. | Electrode | Product | Yield (%) |
|---|---|---|---|---|
| 43 | room temperature | Pt—Pt | 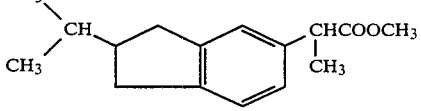 | 80 |
|  |  |  | 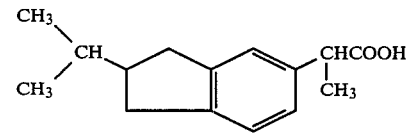 | 7 |
| 44 | room temperature | Pt—Pt | 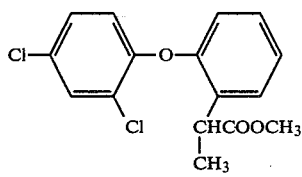 | 72 |
|  |  |  | 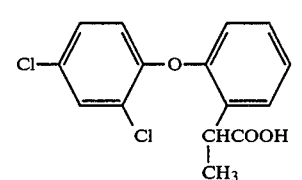 | 8 |
| 45 | room temperature | Pt—Pt | 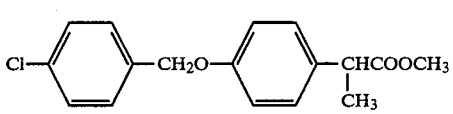 | 81 |
|  |  |  | 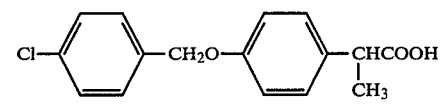 | 10 |

I claim:

1. A process for preparing an α-alkylated acetic acid derivative represented by the formula

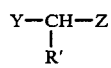     (II)

wherein Z is —COOR or —CN in which R is straight-chain or branched-chain alkyl, cycloalkyl, substituted or unsubstituted phenyl, or substituted or unsubstituted aralkyl, R' is substituted or unsubstituted straight-chain or branched-chain alkyl or alkenyl, and Y is an optionally substituted heterocyclic group or optionally substituted aromatic group, the substituents for the groups represented by Y being at least one species selected from the group consisting of hydroxyl, alkoxy, halogen, nitro, alkyl, alkenyl, alkylthio, alkenylthio, arylthio, heterocyclic thio group, cyclic tertiary amino, dialkylamino, alkenyloxy, substituted or unsubstituted aryl, substituted or unsubstituted aryloxy and substituted or unsubstituted aralkyloxy, the aromatic group or heterocyclic group, when having two or more adjacent substituents, optionally constituting a substituted or unsubstituted fused ring which may contain sulfur, oxygen and/or nitrogen, the process comprising electrolyzing an electrolysis medium consisting essentially of:

(a) a compound of the formula

     (I)

wherein Y and Z are as defined above,
(b) an alkylating agent,
(c) a solvent, and
(d) a supporting electrolyte, thereby effecting electrolytic reduction of the compound of the formula (I) and alkylation of the resulting electrolytic reduction product to produce said α-alkylated acetic acid derivative of formula (II).

2. A process as defined in claim 1 in which R represents straight-chain or branched-chain $C_1$–$C_6$ alkyl, $C_5$–$C_6$ cycloalkyl, unsubstituted phenyl, phenyl substituted with halogen, nitro, $C_1$–$C_5$ alkyl or $C_1$–$C_4$ alkoxy on the phenyl ring, unsubstituted benzyl, benzyl substituted with halogen, nitro, $C_1$–$C_5$ alkyl or $C_1$–$C_4$ alkoxy on the phenyl ring, diphenylmethyl or triphenyl methyl, Y represents a hetrocyclic group selected from the group consisting of thienyl, furyl, pyridyl, pyrolyl, oxazolyl, thiazolyl, thiadiazolyl and pyranyl, or an aromatic group selected from the group consisting of phenyl, naphthyl, anthranyl and tetralyl, the heterocyclic group and the aromatic group being optionally substituted with hydroxyl, $C_1$–$C_6$ alkoxy, halogen-substituted $C_1$–$C_6$ alkoxy, $C_1$–$C_6$ alkyl, $C_3$–$C_6$ alkenyl, nitro, halogen, $C_1$-$C_6$ alkylthio, $C_3$-$C_6$ alkenylthio, unsubstituted phenylthio, phenylthio substituted with $C_1$-$C_4$ alkoxy, nitro or halogen on the phenyl ring, oxazolylthio, thienylthio, thiazolylthio, thiadiazolylthio, pyridylthio, furylthio, 1-oxo-2-isoindolinyl, pyrrolinyl, di($C_1$-$C_6$ alkyl)amino, $C_3$-$C_6$ alkenyloxy, phenyl, phenyl substituted with $C_1$-$C_5$ alkoxy, $C_3$-$C_5$ alkenyloxy, benzyloxy, nitro, halogen, hydroxy, $C_1$-$C_5$ alkyl or $C_1$-$C_2$ alkylenedioxy on the phenyl ring, phenoxy, phenoxy substituted with $C_1$-$C_4$ alkoxy, nitro, halogen or $C_1$-$C_5$ alkyl on the phenyl ring, phenyl-$C_1$-$C_3$ alkyloxy optionally substituted with $C_1$-$C_5$ alkyloxy or halogen on the phenyl ring, diphenylmethyloxy, or Y may also represent a fused ring group selected from the group consisting of benzoxazolyl, benzothiazolyl, dibenzoxepinyl, benzopyranopyridyl, dihydrobenzopyranyl, tetrahydrobenzopyranyl, quinolyl, benzofuranyl, carbazolyl, phenothiazinyl, dihydrodibenzothiepinyl, fluorenyl and indanyl, the fused ring group being optionally substituted with halogen or $C_1$-$C_4$ alkyl.

3. A process as defined in claim 1 in which the alkylating agent is alkyl ester of methanesulfonic acid, mono- or di-alkyl sulfate, alkyl halide, trialkyl phosphate, alkyl ester of benzenesulphonic acid, alkyl orthoformate, 2,2-dialkoxy alkane, aralkyl halide, alkoxyalkyl halide, phenoxyalkyl halide or alkenyl halide.

4. A process as defined in claim 1 in which the alkylating agent is used in an amount of about 1 to about 10 moles per mole of the compound of the formula (I).

5. A process as defined in claim 1 in which the solvent is an aprotic organic polar solvent used singly or in mixture with an inert solvent.

6. A process as defined in claim 1 in which the solvent is at least one aprotic solvent selected from the group consisting of dimethylformamide, dimethylacetamide, acetonitrile, propionitrile, hexamethylphosphoramide and dimethylsulfoxide.

7. A process as defined in claim 6 in which the supporting electrolyte is quaternary ammonium salt, alkali metal salt or alkaline earth metal salt.

8. A process as defined in claim 6 in which the supporting electrolyte contains as an anion component halogen ion, nitrate ion, perchlorate ion, periodate ion, sulfate ion, borofluorate ion or sulfonate ion.

9. A process as defined in claim 6 in which the supporting electrolyte is used in an amount of about 0.01 to about 50 mols per mol of the compound of the formula (I).

10. A process as defined in claim 1 in which the electrolytic reduction is carried out with use of a diaphragm.

11. A process as defined in claim 1 in which the electrolytic reduction is carried out at a temperature of about $-30°$ to about $80°$ C.

* * * * *